United States Patent [19]

Gorman et al.

[11] Patent Number: 4,620,028

[45] Date of Patent: Oct. 28, 1986

[54] ESTERS OF HYDROXYALKYL ETHERS OF BORNANE

[75] Inventors: C. Rodney Gorman, Orange Park; James M. Evans; Sean G. Traynor, both of Jacksonville, all of Fla.

[73] Assignee: SCM Corporation, New York, N.Y.

[21] Appl. No.: 738,230

[22] Filed: May 28, 1985

[51] Int. Cl.$^4$ .............................................. C07C 69/74
[52] U.S. Cl. .................... 560/193; 560/220; 526/282
[58] Field of Search .............. 560/220, 193; 526/282

[56] References Cited

U.S. PATENT DOCUMENTS 3,354,225 11/1967 Kane ...................................... 568/665
4,234,711 11/1980 Emmons et al. .................... 526/282

FOREIGN PATENT DOCUMENTS 939438 6/1980 U.S.S.R. ............................. 560/220

Primary Examiner—Natalie Trousof
Assistant Examiner—L. Hendriksen
Attorney, Agent, or Firm—R. A. Sturges

[57] ABSTRACT

Compounds having the general formula:

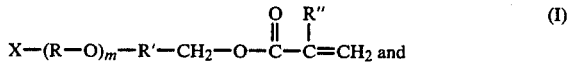

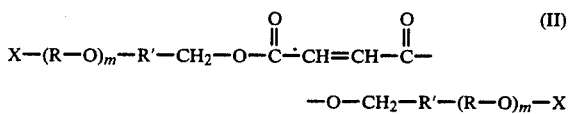

wherein X is the 2-(1,7,7-trimethylbicyclo[2.2.1]hept-2-yl)oxy, R is —(CH$_2$)$_p$— where p varies from 1 to 3; R' is (CH$_2$)$_n$— where n varies from 1 to 7; R'' is hydrogen or methyl; and m is 0 to 4.

11 Claims, No Drawings

ESTERS OF HYDROXYALKYL ETHERS OF BORNANE

This invention relates to esters of hydroxyalkyl ethers of bornane, and more particularly to monounsaturated low molecular weight, e.g., three to four carbon atoms, carboxylic acid esters thereof. A preferred hydroxy alkyl ether is 2-(beta-hydroxyethoxy)bornane. These esters are especially useful in forming homopolymers and copolymers with other polymerizable materials to yield products having molecular weights ranging from 10,000 to 1,000,000 or more. They are also useful as reactive diluents in ultraviolet light or radiation cured printing inks.

BACKGROUND OF THE INVENTION AND PRIOR ART

The useful starting materials have the general formula:

$$X-(R-O)_m-R'-CH_2-OH \qquad (I)$$

wherein X is a 1,7,7-trimethylbicyclo[2.2.1]hept-2-yloxy radical, R is $-(CH_2)_p-$ where p varies from 1 to 3; R' is $-(CH_2)_n-$ where n varies from 1 to 7; and m varies from 0 to 4.

The terpenoid starting materials used in making the esters of this invention and methods for making such starting materials are described in the U.S. Pat. No. 3,354,225 to Kane dated Nov. 21, 1967. This reference is incorporated herein in toto by reference thereto.

BRIEF STATEMENT OF THE INVENTION

Briefly stated, the present invention is a composition of matter having the general formula selected from:

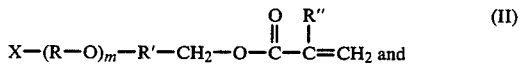
$$X-(R-O)_m-R'-CH_2-O-\overset{O}{\underset{\|}{C}}-\overset{R''}{\underset{|}{C}}=CH_2 \text{ and} \qquad (II)$$

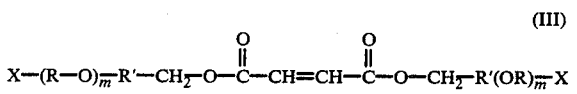
$$X-(R-O)_{\overline{m}}R'-CH_2-O-\overset{O}{\underset{\|}{C}}-CH=CH-\overset{O}{\underset{\|}{C}}-O-CH_2-R'(OR)_{\overline{m}}X \qquad (III)$$

wherein X is the 1,7,7-trimethylbicyclo [2.2.1]hept-2-yloxy radical or isobornyloxy radical, R is $(CH_2)_p-$ where p varies from 1 to 3; R' is $-(CH_2)_n-$ where n varies from 1 to 7, R'' is H or $CH^3$ and m is 0 to 4.

In preferred embodiments of this invention, the esters have the general formula:

$$X-O-R^3-\overset{O}{\underset{\|}{C}}-\overset{R^4}{\underset{|}{C}}=CH_2 \qquad (IV)$$

wherein $R^3$ is an alkylene group containing from 2 to 8 carbon atoms, or a polyoxyalkylene group of 2 to 4 units and where the alkylene group contains 2 to 3 carbon atoms, $R^4$ is hydrogen or methyl, and X is as defined above.

The products of this invention are believed to be novel.

DETAILED DESCRIPTION OF THE INVENTION

The terpenoid starting materials may be derivatives of camphene and have the following general formula:

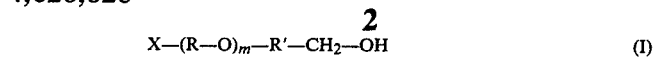
$$X-(R-O)_m-R'-CH_2-OH \qquad (I)$$

They may be synthesized by utilizing the teachings of Kane in U.S. Pat. No. 3,354,225, supra. A preferred class of starting materials has the general formula:

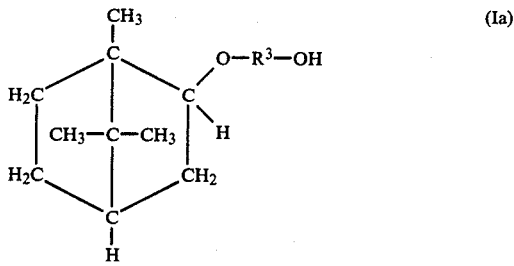

(Ia)

wherein $R^3$ is alkylene containing 2–8 carbon atoms or polyoxyalkylene group of 2 to 4 units wherein the alkylene group contains 2 or 3 carbon atoms, and preferably where the alkylene group is ethylene. Members of this class of starting materials are conveniently reacted with an acrylic acid ester or acrylic acid having the general formula:

$$CH_2=\overset{R''}{\underset{|}{C}}-\overset{O}{\underset{\|}{C}}-O-R^5 \qquad (V)$$

wherein R'' is hydrogen or methyl and $R^5$ is $C_1$–$C_4$ alkyl, or hydrogen.

To form the compounds of structure IV above, the starting materials of structure I or Ia are reacted in proportions such as given below with an acid or ester such as represented by V in the presence of a catalyst. These esters IV may also be prepared by reacting camphene with a hydroxyalkyleneacrylate or with a hydroxyalkylenemethacrylate. Compounds of structure III are formed by the reaction of fumaric acid, fumaryl chloride, or lower alkyl esters of fumaric acid, maleic acid, maleic anhydride, or lower alkyl esters of maleic acid with a starting material of structure I.

Specific illustrative examples of the novel classes of compounds of Structures II and III include, but are not limited to the following:

(a) 2-(1,7,7-trimethylbicyclo[2.2.1]hept-2-yloxy) ethyl 2-propenoate and the corresponding 2-methyl-2-propenoate.

(b) 3-(1,7,7-trimethylbicyclo[2.2.1]hept-2-yloxy)propyl-2-propenoate and the corresponding 2-methyl-2-propenoate.

(c) 6-(1,7,7-trimethylbicyclo[2.2.1]hept-2-yloxy)hexyl-2-propenoate and the corresponding 2-methyl-2-propenoate.

(d) 8-(1,7,7-trimethylbicyclo[2.2.1]hept-2-yloxy)octyl-2-propenoate and the corresponding 2-methyl-2-propenoate.

(e) 2-(2-(1,7,7-trimethylbicyclo[2.2.1]hept-2-yloxyethoxy) ethyl-2-propenoate and the corresponding 2-methyl-2-propenoate.

(f) 3-(3-(1,7,7-trimethylbicyclo[2.2.1]hept-2-yloxy)-propoxy)propyl-2-propenoate and the corresponding 2-methyl-2-propenoate.

(g) 2-(1,7,7-trimethylbicyclo[2.2.1]hept-2-yloxy)ethoxy(ethoxy)$_n$-ethyl-2-propenoate and the corresponding 2-methyl-2-propenoate, where n=1 to 3.

(h) bis(2,(1,7,7-trimethylbicyclo[2.2.1]hept-2-yloxy)-ethyl)fumarate and the corresponding maleate diester.

(i) 2-(1,7,7-trimethylbicyclo[2.2.1]hept-2-yloxy) (polyethoxy)$_n$-2-propenoate and the corresponding 2-methyl-2-propenoate, and where n is 2, or 3, or 4.

Suitable procedures are exemplified below. In the following examples, temperatures are in degrees Centigrade, and "g"=grams.

EXAMPLE 1

2-(1,7,7-trimethylbicyclo[2.2.1]hept-2-yloxy)ethyl-2-propenoate (IX) was prepared by trans-esterification of 2-(Beta-hydroxyethoxy)-bornane (VII) with ethyl acrylate (VIII) using tetraisopropyl titanate catalyst. 125 g. of (VII), 221 g. ethyl acrylate (VIII), 0.90 g. phenothiazine, and 0.23 g. nitrobenzene were charged to a 500 ml. glass reactor equipped with magnetic stirrer, thermometer, 1"×12" packed column (stainless steel Pro-Pac) and a distillation head equipped with a reflux control connected to a timer and temperature controller. A nitrogen stream was maintained in the condenser to prevent moisture from entering the system. The reactor was heated to reflux to remove any water as an ethanol/water azeotrope. After 2 hours refluxing, the reaction was cooled to 30° and 1.0 g. of tetraisopropyl titanante was added to the still pot. The reaction was heated to reflux at atmospheric pressure and ethanol removed as formed as its azeotrope with ethylacrylate up to 88° C. boiling range. When the boiling range reached 100° C. at atm., a cut was taken at 100 mm to 125° pot, then 10 mm to 125° pot. The product (IX) was distilled at 1 mm to 180° pot. 113 g. product (IX) analyzing at 98.4% by VPC was obtained. Structure was verified by NMR. Theory yield was 71%.

This example is the best mode of carrying out our invention in terms of the product per se and the process of making it.

EXAMPLE 2

The methacrylate (X) corresponding to (IX) above was prepared by trans-esterification of 2-betahydroxyethoxy)-camphene (VII) with methyl methacrylate (XI) using tetraisopropyl titanate catalyst.

The equipment was the same as used in Example 1 with 150 g. (VII), 265 g. methyl methacrylate (XI), 1.08 g. phenolthiazine, 0.28 g. nitro benzene charged to starting pot and refluxed to remove any water as water/methanol azeotrope. After adding 1.1 g. tetraisopropyl titanate catalyst, the methanol was removed as methanol/methyl methacrylate azeotrope to 100° boiling range at atmospheric pressure. 30 g. of product (X) were distilled overhead at 175°-200° C./1 mm. The distilled product (X) analyzed as 95.3%; structure was verified by NMR. The balance of the product (X) remained in the pot and contained some polymer by GPC.

EXAMPLE 3

Product (IX) above was prepared by reaction of camphene with hydroxyethylacrylate (XII) (HEA) using Amberlyst 15 resin as catalyst.

200 g. Camphene (94% tricyclene+camphene), 0.04 g. p-methoxyphenol, 128 g. hydroxyethylacrylate (XII), 15 g. Amberlyst 15 (A-15; CA Reg. No. 9037-24-5) resin were charged to a 500 ml. glass reactor and stirred at 25°-30° C. for 24 hours. VPC analysis of a filtered sample was 36.1% camphene+tricyclene, 54.3% Product IX above.

EXAMPLE 4

Product (X) above (the methacrylate) was prepared by reaction of camphene with hydroxyethylmethacrylate (XIII) (HEMA) using Amberlyst 15 (A-15) resin as catalyst.

200 g. camphene (94% camphene+tricyclene), 0.04 g. p-methoxyphenol, 143 g. HEMA, and 15 g. A-15 resin were charged to a 500 ml. glass reactor and stirred at 25°-30° C. for 24 hours. Analysis of a filtered sample was 21.6% camphene+tricyclene and 69.1% Product (X).

The compounds of this invention may be used to form homopolymers and copolymers. Especially useful are the copolymers of the acrylates and methacrylates [(a) above] with vinyl acetate. Such polymers may be used for coatings, printing inks, adhesives, etc., having molecular weights in the range of 10,000 to 1,000,000. Solution polymerization or emulsion polymerization may be used. The compositions hereof in the monomeric state may be used as reactive diluents for ultraviolet and other radiation or electron beam cured inks, coatings and adhesives. The novel compounds have good solvency power, their toxicity is low, their volatility is low, and they are reactive.

What is claimed is:

1. A compound having a general formula selected from:

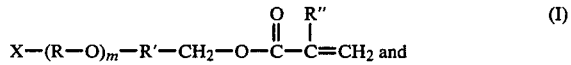

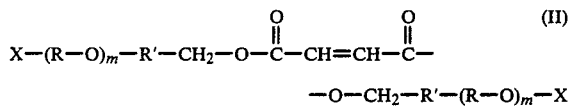

wherein X is [2-(1,7,7-trimethylbicyclo[2.2.1]hept-2-ylo)oxy]1,7,7-trimethylbicyclo[2.2.1]hept-2-yloxy radical, R is —(CH$_2$)$_p$— where p varies from 1 to 3; R' is —(CH$_2$)$_n$— where n varies from 1 to 7; R" is hydrogen or methyl; and m is 0 to 4.

2. A compound having the general formula:

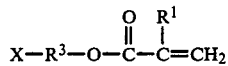

wherein X is 1,7,7-trimethylbicyclo[2.2.1]hept-2-yloxy [2-(1,7,7-trimethylbicyclo[2.2.1]hept-2-ylo)oxy], R$^3$ is an alkylene group containing from 2 to 8 carbon atoms, or a polyoxyalkylene group of 2 to 4 units and where the alkylene group contains 2 to 3 carbon atoms, and R$^1$ is hydrogen or methyl.

3. A compound as defined in claim 2 wherein R$^3$ is ethylene.

4. A compound as defined in claim 2 wherein R$^3$ is propylene.

5. A compound as defined in claim 2 wherein R$^1$ is methyl.

6. A compound as defined in claim 2 wherein R$^3$ is ethylene and R$^1$ is methyl.

7. A compound as defined in claim 2 wherein R$^3$ is propylene and R$^1$ is methyl.

8. A compound as defined in claim 2 wherein R$^3$ is hexamethylene.

9. Bis(2-(1,7,7-trimethylbicyclo[2.2.1]hept-2-yloxy)ethyl)fumarate.

10. 2-(1,7,7-Trimethylbicyclo[2.2.1]hept-2-yloxy)ethyl2-propenoate.

11. 2-(1,7,7-Trimethylbicyclo[2.2.1.]hept-2-yloxy)ethyl2-methyl-2-propenoate.

* * * * *